United States Patent [19]
Robinson

[11] Patent Number: 5,607,959
[45] Date of Patent: Mar. 4, 1997

[54] OXINDOLE 1-[N-(ALKOXYCARBONYL)] CARBOXAMIDES AND 1-(N-CARBOXAMIDO) CARBOXAMIDES AS ANTIINFLAMMATORY AGENTS

[75] Inventor: Ralph P. Robinson, Gales Ferry, Conn.

[73] Assignee: Pfizer Inc., New York, N.Y.

[21] Appl. No.: 495,509

[22] PCT Filed: Dec. 10, 1993

[86] PCT No.: PCT/US93/11792

§ 371 Date: Jul. 21, 1995

§ 102(e) Date: Jul. 21, 1995

[87] PCT Pub. No.: WO94/18194

PCT Pub. Date: Aug. 18, 1994

Related U.S. Application Data

[63] Continuation of Ser. No. 15,144, Feb. 9, 1993, abandoned.

[51] Int. Cl.[6] .................. C07D 409/06; A61K 31/40
[52] U.S. Cl. .................. 514/414; 514/418; 548/468; 548/486; 548/312.1; 546/277.7
[58] Field of Search .................. 514/414, 418; 548/468, 486

[56] References Cited

U.S. PATENT DOCUMENTS 4,556,672  12/1985  Kadin .
4,569,942  2/1986  Kadin .
4,658,037  4/1987  Kadin .
4,721,712  1/1988  Kadin .
4,952,703  8/1990  Kelly .
5,118,703  6/1992  Reiter .
5,270,331  12/1993  Barth .

FOREIGN PATENT DOCUMENTS 0153818  2/1985  European Pat. Off. .
0365194  10/1989  European Pat. Off. .
0393936  10/1990  European Pat. Off. .

*Primary Examiner*—Jacqueline Haley
*Attorney, Agent, or Firm*—Peter C. Richardson; Gregg C. Benson; Mervin E. Brokke

[57] ABSTRACT

Compounds of formula (I) where $R^1$ is thienyl, phenyl or furyl, X and Y are halogen or hydrogen and Q is alkoxy or amino are useful as analgesic and antiinflamatory agents.

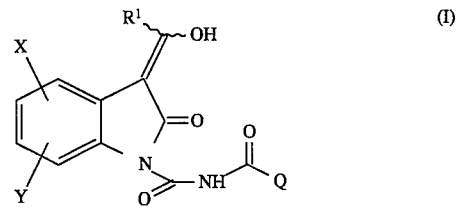

15 Claims, No Drawings

OXINDOLE 1-[N-(ALKOXYCARBONYL)] CARBOXAMIDES AND 1-(N-CARBOXAMIDO) CARBOXAMIDES AS ANTIINFLAMMATORY AGENTS

This application is the National Phase of International Application PCT/US93/11792 filed Dec. 10, 1993 now WO94/18194 which is a continuation of U.S. application Ser. No. 08/015,144, filed Feb. 9, 1993, now abandoned.

BACKGROUND OF THE INVENTION

The present invention is concerned with analgesic and antiinflammatory agents and, in particular, with oxindole-1-[N-(alkoxycarbonyl)]carboxamides and 1-(N-carboxamido)carboxamides as antiinflammatory agents.

The use of oxindoles as antiinflammatory agents has been reported in U.S. Pat. No. 3,634,453 which claimed 1-substituted-2-oxindole-3-carboxamides. Recently, a series of 3-acyl-2-oxindole-1-carboxamides was disclosed in U.S. Pat. No. 4,556,672 and U.S. Pat. No. 4,569,942 to be inhibitors of the cyclooxygenase (CO) and lipoxygenase (LO) enzymes and to be useful as analgesic and antiinflammatory agents in mammalian subjects.

U.S. Pat. No. 4,658,037 provides novel 2-oxindole compounds of the formula

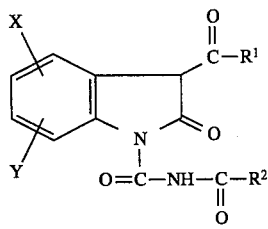

and the pharmaceutically-acceptable base salts thereof; wherein

X is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons, trifluoromethyl, alkylsulfinyl having 1 to 4 carbons, alkylsulfonyl having 1 to 4 carbons, nitro, phenyl, alkanoyl having 2 to 4 carbons, benzoyl, thenoyl, alkanamido having 2 to 4 carbons, benzamido and N,N-dialkylsulfamoyl having 1 to 3 carbons in each of said alkyls; and Y is selected from the group consisting of hydrogen, fluoro, chloro, bromo, alkyl having 1 to 4 carbons, cycloalkyl having 3 to 7 carbons, alkoxy having 1 to 4 carbons, alkylthio having 1 to 4 carbons and trifluoromethyl;

or X and Y when taken together are a 4,5-, 5,6-or 6,7-methylenedioxy group or a 4,5-, 5,5- or 6,7-ethylenedioxy group; or X and Y when taken together and when attached to adjacent carbon atoms, form a divalent radical Z, wherein Z is selected from the group consisting of

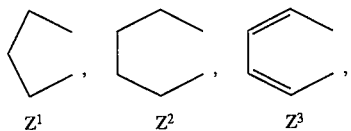

-continued

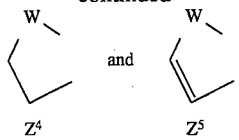

wherein W is oxygen or sulfur;

$R^1$ is selected from the group consisting of alkyl having 1 to 6 carbons, cycloalkyl having 3 to 7 carbons, phenyl, substituted phenyl, phenylalkyl having 1 to 3 carbons in said alkyl, (substituted phenyl)alkyl having 1 to 3 carbons in said alkyl, phenoxyalkyl having 1 to 3 carbons in said alkyl, (substituted phenoxy)alkyl having 1 to 3 carbons in said alkyl, naphthyl and $—(CH_2)_n—Q—R^0$;

wherein the substituent on said substituted phenyl, said (substituted phenyl)alkyl and said (substituted phenoxy)alkyl is selected from the group consisting of fluoro, chloro, alkyl having 1 to 3 carbons, alkoxy having 1 to 3 carbons and trifluoromethyl; n is zero, 1 or 2; Q is a divalent radical derived from a compound selected from the group consisting of furan, thiophene, pyrrole, thiazole, isothiazole, oxazole, isoxazole, 1,2,3-thiadiazole, 1,2,5-thiadiazole, tetrahydrofuran, tetrahydrothiophene, pyridine, pyrimidine, pyrazine, benzo[b-]furan and benzo[b]thiophene; and $R^0$ is hydrogen or alkyl having 1 to 3 carbons;

and $R^2$ is selected from the group consisting of alkyl having 1 to 6 carbons, cycloalkyl having 3 to 7 carbons, phenoxymethyl, furyl, thienyl, pyridyl and

wherein $R^3$ and $R^4$ are each selected from the group consisting of hydrogen, fluoro, chloro, alkyl having 1 to 4 carbons, alkoxy having 1 to 4 carbons and trifluoromethyl.

Certain prodrugs of 3-acyl-2-oxindoles-1-carboxamides are described in commonly owned U.S. Pat. No. 5,118,703 which are of the formula:

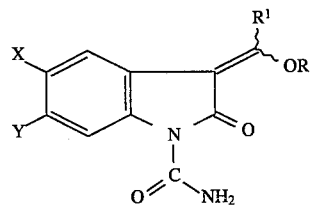

wherein X and Y are each hydrogen, fluoro or chloro; $R^1$ is 2-thienyl or benzyl; and R is alkanoyl of two to ten carbon atoms, cycloalkylcarbonyl of five to seven carbon atoms, phenylalkanoyl of seven to ten carbon atoms, chlorobenzoyl, methoxybenzoyl, thenoyl, omega alkoxycarbonylalkanoyl said alkoxy having one to three carbon atoms and said alkanoyl having three to five carbon atoms; alkoxy carbonyl of two to ten carbon atoms; phenoxycarbonyl; 1-(acyloxy)alkyl said acyl having one to four carbon atoms; 1-(alkoxycarbonyloxy)alkyl said alkoxy having two to five carbon atoms and said alkyl having one to four carbon atoms; alkyl of one to three carbon atoms; alkylsulfonyl of one to three carbon atoms; methylphenylsulfonyl or dialkylphosphonate said alkyl each of one to three carbon atoms.

Commonly owned copending U.S. Pat. No. 5,270,331 discloses compounds of the formula

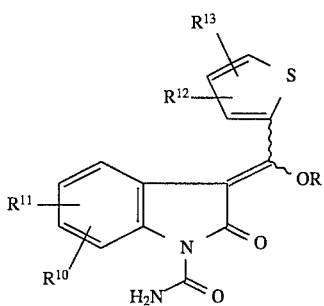

wherein $R^{10}$, $R^{11}$, $R^{12}$ and $R^{13}$ are hydrogen, alkyl or halogen and R is methyleneoxyalkanoyl, methyleneoxyalkenoyl or alkenoyl.

U.S. Pat. Nos. 4,556,672, 4,658,037, 4,569,942, 5,270,331 and 5,118,703 are hereby incorporated by reference.

SUMMARY OF THE INVENTION

The present invention provides analgesic and antiinflammatory oxindoles of the formula

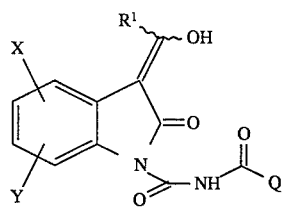

I wherein,

X is chlorine or fluorine;

Y is hydrogen, chlorine or fluorine;

$R^1$ is substituted or unsubstituted thienyl, furyl or phenyl;

Q is $OR^2$ or $NR^3R^4$; wherein $R^2$ is $C_1$–$C_{10}$ alkyl, $C_4$–$C_{10}$ cycloalkyl, phenyl, substituted phenyl, $C_5$–$C_{10}$ cycloalkenyl, $C_3$–$C_{10}$ alkenyl, $(CH_2)_m CH(R^5)CO_2R^6$, $(CH_2)_m CH(R^5)CONR^6R^7$, $(CH_2)_n CH(R^8)NR^5R^9$, farnesyl, geranyl, 6-indanyl, $CH_2(2,2$-dimethyl-1,3-dioxolan-4-yl), $(CH_2)_n$-2-thienyl, $(CH_2)_n$-3-thienyl, $(CH_2)_n$-3-furyl, $(CH_2)_n$-2-furyl, $(CH_2)_n$-2-pyridyl, $(CH_2)_n$-3-pyridyl, $(CH_2)_n$-4-pyridyl, $(CH_2)_n$-phenyl or $(CH_2)_n$-substituted phenyl;

$R^3$ is hydrogen, $OR^5$, $C_1$–$C_{10}$ alkyl, $C_4$–$C_{10}$ cycloalkyl, phenyl, substituted phenyl, $C_3$–$C_{10}$ alkenyl, $C_5$–$C_{10}$ cycloalkenyl, $(CH_2)_m CH(R^{10})CO_2R^5$, $(CH_2)_y NR^5R^9$, $(CH_2)_n$-phenyl, $(CH_2)_n$-substituted phenyl, $(CH_2)_n$-3-thienyl, $(CH_2)_n$-2-thienyl, $(CH_2)_n$-2-furyl, $(CH_2)_n$-3-furyl, $(CH_2)_n$-2-pyridyl, $(CH_2)_n$-3-pyridyl, or $(CH_2)_n$-4-pyridyl;

$R^4$ is hydrogen, $C_1$–$C_{10}$ alkyl, $C_4$–$C_{10}$ cycloalkyl, phenyl, substituted phenyl, $C_3$–$C_{10}$ alkenyl, $C_5$–$C_{10}$ cycloalkenyl, $(CH_2)_y NR^5R^9$, $(CH_2)_n$-phenyl, $(CH_2)_n$-substituted phenyl, $(CH_2)_n$-2-thienyl, $(CH_2)_n$-3-thienyl, $(CH_2)_n$-2-furyl, $(CH_2)_n$-3-furyl, $(CH_2)_n$-2-pyridyl, $(CH_2)_n$-3-pyridyl, or $(CH_2)_n$-4-pyridyl;

$R^5$, $R^6$ and $R^7$ are independently hydrogen, $C_1$–$C_6$ alkyl, benzyl, phenyl, allyl, $C_4$–$C_8$ cycloalkyl;

$R^8$ is hydrogen, $R^5$, $CO_2R^5$ or $CONR^5R^6$;

$R^9$ is $R^5$, $C_1$–$C_6$ alkyl carbonyl, benzoyl, substituted benzoyl, benzyloxycarbonyl, or $C_1$–$C_6$ alkoxycarbonyl;

$R^{10}$ is $C_1$–$C_6$ alkyl, $(CH_2)_n NR^5R^9$, $CH(CH_3)OR^5$, $CH_2OR^5$, $CH_2$-3-indolyl, $CH_2SR^5$, $CH_2$-p-$C_6H_4OR^5$, $(CH_2)_n SR^6$ or $(CH_2)_n$-3-imidazolyl;

m is 0–6; n is 1–6; and y is 2–6; or a pharmaceutically acceptable salt thereof.

A preferred group of compounds are those of formula I wherein X is 5-chloro and Y is hydrogen.

A second preferred group of compounds are those of formula I wherein X is 5-fluoro, Y is 6-chloro and $R^1$ is 2-thienyl.

A third preferred group of compounds are those of formula I wherein X is 5-fluoro, Y is 6-chloro, $R^1$ is 2-thienyl and Q is $OR^2$ wherein $R^2$ is alkyl, benzyl or $(CH_2)_m CH(NHR^7)COOR^5$ wherein m is one, and $R^5$ and $R^7$ are hydrogen.

A fourth preferred group of compounds are those of formula I wherein X is 5-fluoro, Y is 6-chloro, $R^1$ is 2-thienyl and Q is $N(OR^3)R^6$. Especially preferred within this group are the compounds wherein $R^3$ is hydrogen.

A fifth preferred group of compounds are those of formula I wherein X is 5-fluoro, Y is 6-chloro, $R^1$ is 2-thienyl and Q is $NR^2R^3$. Especially preferred within this group are those compounds wherein $R^2$ is $C_1$–$C_6$ alkyl or benzyl and $R^3$ is hydrogen or $C_1$–$C_6$ alkyl.

The present invention also comprises a method for treating pain or inflammation in a mammal which comprises administering to said mammal an analgesic or an antiinflammatory effective amount of a compound selected from those of formula (I).

The present invention further comprises a pharmaceutical composition comprising an effective amount of a compound of formula (I) and a pharmaceutically acceptable carrier.

DETAILED DESCRIPTION OF THE INVENTION

In converting the 3-acyl-2-oxindoles to the compounds of formula I, the substituents on the exocyclic double bond at the 3-position can be syn, anti or a mixture of both. Thus, the compounds of the structures

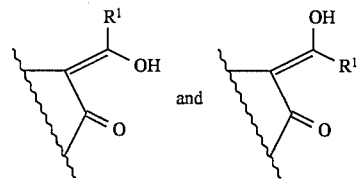

of mixtures thereof are depicted as

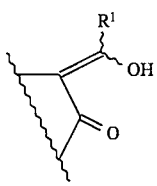

These compounds may also exist in the tautomeric keto form

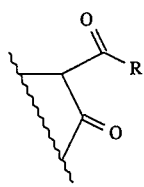

All forms of these isomers are considered part of the present invention.

Alkyl groups are defined according to the number of carbon atoms therein. The alkyl chains may be either linear or branched.

This invention contemplates that phenyl and heterocyclic groups may be unsubstituted or optionally substituted with one to three substituents independently selected from $C_1$–$C_6$ alkyl, $C_1$–$C_6$ alkoxy, $C_1$–$C_6$ haloalkoxy, halogen, nitro, carboxy carboalkoxy, carboxamide, amino or $C_1$–$C_6$ alkylmercapto.

The compounds of the present invention are prepared by the reactions shown below.

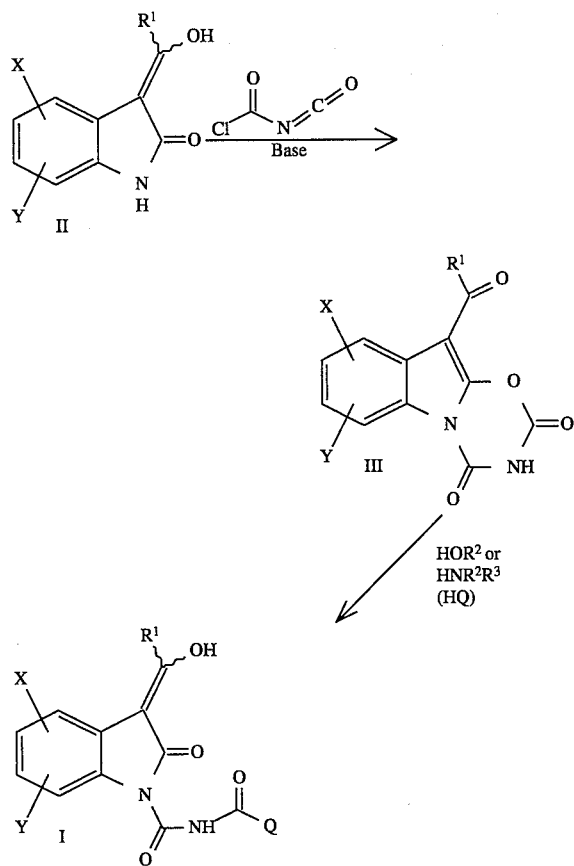

The starting materials for the synthesis of compounds of formula I are the acyl oxindole derivatives II which are prepared as disclosed in U.S. Pat. Nos. 4,556,672, 4,569,942 and 4,658,037.

A solution or suspension of the acyl oxindole derivative II and 1 to 2 equivalents (preferably 1.1 equivalents) of triethylamine (the base) in methylene chloride is cooled in an ice bath. A solution of chlorocarbonyl isocyanate (1 to 1.1 equivalents) is then added dropwise with stirring. The resulting mixture is stirred at 0° C. for 1 hour and then at 25° C. overnight. The product (III) is then collected by filtration, washed with methylene chloride and recrystallized. Alternative solvents for the reaction are those which will not react with chlorocarbonyl isocyanate, for example, chloroform, carbon tetrachloride, 1,2-dichloroethane, benzene, toluene, tetrahydrofuran, diethyl ether and 1,2-dimethoxyethane. Reaction temperatures may vary between −78° C. and the boiling point of the solvent used. Reaction times may vary between 1 minute and several days depending on the temperature used. Other bases which may be used in the reaction in place of triethylamine are tertiary mines which will not react with chlorocarbonyl isocyanate including pyridine, 4-(dimethylamino)pyridine, 2,6-lutidine and diazabicycloundecene (DBU).

In the second step of the sequence, the intermediate III is reacted with an alcohol ($HOR^2$) or and amine ($HNR^2R^3$) as follows:

For reaction with an alcohol, the compound III is dissolved or slurried in the alcohol $HOR^2$ (1 or more equivalents, preferably 10 or more equivalents). The mixture is cooled in an ice bath and triethylamine (1 to 10 equivalents, preferably 1.1 equivalents) is added dropwise with stirring. The reaction is stirred at 25° C. overnight and at this time, is diluted with methylene chloride (or some other suitable, water-immiscible solvent, e.g. chloroform). The resulting solution is washed with 1N HCl solution and brine and then dried over magnesium sulfate. The solution is then distilled in vacuo to remove methylene chloride and any excess alcohol leaving the crude product I ($Q=OR^2$) typically as a yellow solid. Purification is by trituration, recrystallization and/or flash chromatography. Reaction temperatures may vary between −20° and 80° C. Reaction times may vary between 15 minutes and several days depending on the temperature used. Other bases which may be used in the reaction in place of triethylamine are tertian/amines which will not react directly with Compound III. These include pyridine, 4-(dimethylamino)pyridine, 2,6-lutidine and diazabicycloundecene (DBU). In certain instances it is preferable to run the reaction in an inert solvent such as methylene chloride, toluene, chloroform, dioxane or 1,2-dimethoxyethane using 1 to 10 equivalents of the alcohol, Here, workup is the same as those reactions carded out without a solvent. In other instances (e.g. when $R^2$ is phenyl), it is preferable to use the sodium salt of the alcohol and no added base in the reaction. An inert solvent is required for this variation of the reaction: ether, tetrahydrofuran or 1,2-dimethoxyethane are particularly suitable; the workup is again the same as described above. Alcohols ($R^2OH$) also containing a primary or secondary amino function cannot be used in this reaction as the amino group will react with Compound III first. Thus, the reaction is carried out with a derivative of the amino alcohol suitably protected on the nitrogen. Acceptable protecting groups include carbobenzyloxy (CBZ) (removed by catalytic hydrogenation), t-butoxycarbonyl (BOC) (removed with acid) and 2,2,2-trichloroethoxycarbonyl (TROC) (removed with zinc in acetic acid). The removal of these protecting groups is achieved via standard procedures in the chemical literature well known to those skilled in the art.

For reaction with an amine, the compound III is dissolved in methylene chloride and treated dropwise with 1 to 5 equivalents (preferably 1.1 equivalents) of the amine ($HNR^2R^3$). The reaction is stirred for 2 hr at 25° C. and then poured into 1N HCl solution. The resulting mixture is extracted with methylene chloride (or some other suitable water-immiscible solvent, e.g. chloroform). The extracts are combined, dried over magnesium surfate and concentrated to leave the compound of formula I ($Q=NR^2R^3$) typically as a yellow solid. Purification is by trituration, recrystallization and/or flash chromatography. Reaction temperatures may vary between −78° and 80° C. Reaction times may vary between 15 minutes and several days depending on the temperature used. Alternative solvents for the reaction are those which will not react with Compound III such as methylene chloride, toluene, chloroform, dioxane or 1,2-dimethoxyethane. In instances where the amine $HNR^2R^3$ also contains an acidic group such as carboxyl, the reaction is run in the presence of an equivalent amount (relative to the amount of $HNR^2R^3$ used) of triethylamine. Other bases which may be used in the reaction in place of triethylamine are tertiary amines which will not react directly with Compound III. These include pyridine, 4-(dimethylamino)pyridine, 2,6-lutidine and diazabicycloundecene (DBU).

The compounds of the formula I are acidic and they form base salts. All such base salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, as appropriate, or, in the case of aqueous solutions, by lyophilization. Typical salts of the compounds of formula I which can be prepared are primary, secondary and tertiary amine salts, alkali metal salts and alkaline earth metal salts. Especially valuable are the ethanolamine, diethanolamine and triethanolamine salts.

Basic agents suitably employed in salt formation belong to both the organic and inorganic types, and they include organic amines, alkali metal hydroxides, alkali metal carbonates, alkali metal bicarbonates, alkali metal hydrides, alkali metal alkoxides, alkaline earth metal hydroxides, alkaline earth metal carbonates, alkaline earth metal hydrides and alkaline earth metal alkoxides. Representative examples of such bases are primary amines, such as n-propylamine, n-butylamine, aniline, cyclohexylamine, benzylamine, p-toluidine, ethanolamine and glucamine; secondary amines, such as diethylamine, diethanolamine, N-methylglucamine, N-methylaniline, morpholine, pyrrolidine and piperidine; tertiary amines, such as triethylamine, triethanolamine, N,N-dimethylaniline, N-ethylpiperidine and N-methylmorpholine; hydroxides, such as sodium hydroxide; alkoxides, such as sodium ethoxide and potassium methoxide; hydrides, such as calcium hydride and sodium hydride; and carbonates, such as potassium carbonate and sodium carbonate.

The compounds of formula I possess analgesic activity. This activity is demonstrated in mice by showing blockade of the abdominal stretching induced by administration of 2-phenyl-1,4-benzoquinone (PBQ). The method is based on that of Siegmund et al., *Proc. Soc. Exp. Biol. Med.*, 95: 729–731, 1957, as adapted for high throughput (see further Milne and Twomey, *Agents and Actions*, 10: 31–37, 1980). The mice used in these experiments are Carworth males, albino CF-1 strain, weighing 18–20 g. All mice are fasted overnight prior to drug administration and testing.

The compounds of formula I are dissolved or suspended in a vehicle consisting of ethanol (5%), emulphor 620 (a mixture of polyoxyethylene fatty acid esters, 5%) and saline (90%). This vehicle also serves as control. Doses are on a logarithmic scale (i.e., . . . 0.32, 1.0, 3.2, 10, 32 . . . mg/kg), and are calculated from weights of the salt when applicable, and not of the acid. The route of administration is oral, with concentrations varied to allow a constant dosage volume of 10 ml/kg of body weight. The aforesaid method Milne and Twomey is used to determine efficacy and potency. Mice are treated with compounds orally, and one hour later receive PBQ, 2 mg/kg, intraperitoneally. Individual mice are then immediately placed in a warmed Lucite (transparent plastic) chamber, and, starting five minutes after PBQ administration, the number of abdominal constrictions during the subsequent 5 minutes are recorded. The degree of analgesic protection (% MPE) is calculated on the basis of suppression of abdominal constriction relative to counts from concurrent control animals run on the same day. At least four such determinations (N≧) provide dose-response data for generation of an $MPE_{50}$, the best estimate of the dose that reduces abdominal constriction to 50% of control levels.

The compounds of formula i also possess antiinflammatory activity. This activity is demonstrated in rats by a method based on the standard carrageen-induced rat-foot edema test. (Winter et al., *Proc. Soc. Exp. Biol. Med.*, 111: 544, 1963).

Unanesthetized, adult, male, albino rats of 150 g to 190 g body weight are numbered, weighed, and an ink mark placed on the right lateral malleolus. Each paw is immersed in mercury exactly to the ink mark. The mercury is contained in a glass cylinder, connected to a Statham Pressure Transducer. The output from the transducer is fed through a control unit to a microvoltometer. The volume of mercury displaced by the immersed paw is read. Drugs are given by oral gavage. One hour after drug administration, edema is induced by injection of 0.05 ml of 1% solution of carrageenin into the plantar tissue of the marked paws. Immediately thereafter, the volume of the injected foot is measured. The increase in foot volume 3 hours after the injection of carrageenin constitutes the individual inflammatory response.

The ability of the compounds of formula (I) to inhibit prostaglandin $H_2$ synthase and 5-lipoxygenase may be determined by the following assay procedure. By this procedure, the levels of known products of prostaglandin $H_2$ synthase and 5-lipoxygenase are measured for cells treated with the compound under study with inhibition of prostaglandin $H_2$ synthase and/or 5-lipoxygenase being evidenced by a decrease in the amount of, or absence of, the known products of those enzymes.

RBL-1 cells, maintained in monolayer, are grown for 1 to 2 days in Spinner culture in Minimum Essential Medium (Eagle) with Earle's Salts plus 15% fetal bovine serum supplemented with antibiotic/antimycotic solution (Gibco) according to the method of Jakschlk, B. A,, et al., Nature 287:51–52 (1980). The cells are washed twice and resuspended in cold RPMI 1640 to a cell density of $4\times10^6$ cells/ml. Then, a 0.25 ml aliquot of the compound under study at the desired concentration in RPMI 1640 is equilibrated at 37° C. for 5 minutes. To the equilibrated aliquot is added a 0.25 ml aliquot of prewarmed cell suspension and the mixture is incubated at 37° C. for 5 minutes. A 10 μl solution containing $^{14}C$-arachidonic acid and A-23187 (calcium ionophore, Sigma Chemical) is added and the mixture is incubated at 37° C. for another 5 minutes. Then, 267 μl of acetonitrile/0.3% acetic acid is added and the mixture is allowed to stand on ice for 30 minutes. The tube containing the mixture is vortexed, clarified by centrifugation (300 rpm, 10 minutes) and the supernatant is decanted and re-centrifuged for 2 minutes in a microfuge at high speed. A 100 μl aliquot of the supernatant then is analyzed by HPLC on a Perkin Elmer-HS (3 micron) column using a gradient solvent system of acetonitrile/$H_2$O with 0.1% trifluoroacetic acid and a flow rate of 2 ml/min, Radioactivity detection is accomplished with a Berthold LB504 Radioactivity Monitor equipped with an 800 μl flow cell mixing 2.4 ml/min of OMNIFLUOR (Trademark of New England Nuclear, Boston, Mass.) with the column effluent. Quantitation of the eluted radioactivity is carded out by the use of a Spectra Physics SP4200 imputing integrator. The data so obtained is used in a data-reduction program where the integration units for each product are calculated as percent of the total integration units and compared to average control levels.

The analgesic activity of the compounds of formula I makes them useful for acute administration to mammals for the control of pain, e.g., post-operative pain and the pain of trauma. Additionally the compounds of formula I are useful for chronic administration to mammals for the alleviation of the symptoms of chronic diseases, such as the inflammation of rheumatoid arthritis, and the pain associated with osteoarthritis and other musculoskeletal disorders.

When a compound of the formula I or a pharmaceutically acceptable salt thereof is to be used as either an analgesic agent or an anti-inflammatory agent, it can be administered to a mammalian subject either alone, or, preferably, in combination with pharmaceutically-acceptable careers or diluents in a pharmaceutical composition, according to standard pharmaceutical practice. A compound can be administered orally or parenterally. Parenteral administration includes intravenous, intramuscular, intraperitoneal, subcutaneous and topical administration.

In a pharmaceutical composition comprising a compound of formula I, or a pharmaceutically-acceptable salt thereof, the weight ratio of carrier to active ingredient will normally be in the range from 1:4 to 4:1, and preferably 1:2 to 2:1. However, in any given case, the ratio chosen will depend on such factors as the solubility of the active component, the dosage contemplated and the precise route of administration.

For oral use of a compound of formula I of this invention, the compound can be administered, for example, in the form of tablets or capsules, or as an aqueous solution or suspension. In the case of tablets for oral use, camera which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic.

When a compound of formula I or salt thereof is used in a human subject, the daily dosage will normally be determined by the prescribing physician. Moreover, the dosage will vary according to the age, weight and response of the individual patient, as well as the severity of the patient's symptoms and the potency of the particular compound being administered. However, for acute administration to relieve pain, an effective analgesic response eliciting dose in most instances will be 0.1 to 1.0 g as needed (e.g., every four to six hours). For chronic administration to alleviate (treat) inflammation and pain, in most instances an effective dose will be from 0.5 to 3.0 g per day, and preferably 0.5 to 1.5 g per day, in single or divided doses. On the other hand, it may be necessary to use dosages outside these limits in some cases.

The following examples and preparations are being provided solely for the purpose of further illustration.

EXAMPLES

All reactions were carried out in dry glassware under an atmosphere of nitrogen. The $^1$H nmr spectra were recorded at 300 MHz. The IR spectra were recorded using potassium bromide pellets. All melting points are uncorrected.

Example 1

Compound III, X=5-Cl, Y=H, R$^1$=2-Thienyl

A solution of 5-chloro-3-(2-thenoyl)-2-oxindole (Preparation 1) (11.8 g, 0.042 mol) and triethylamine (5.8 ml, 0.042 mol) in anhydrous methylene chloride (780 ml) was cooled in an ice bath. A solution of chlorocarbonyl isocyanate (3.4 ml, 0.042 mol) in anhydrous methylene chloride (20 ml) was then added dropwise with stirring. When addition of the chlorocarbonyl isocyanate solution was complete, stirring was continued at 20° C. for 18 hours. The mixture was filtered, washing well with methylene chloride, to collect the off-white, finely crystalline title product, 11.0 g 97.6%), mp>250° C.; ir (potassium bromide): v CO 1815, 1805, 1780 cm$^{-1}$; $^1$H nmr (perdeutedoacetone); δ7.27 (dd, 1 H, J=4.0, 5.0 Hz), 7.45 (dd, 1 H, J=2.2, 8.8 Hz), 7.99 (dd, 1 H, J=1.1, 5.0 Hz), 8.04 (d, 1H, J=2.2 Hz), 8.11 (dd, 1 H, J=1.1, 4.0 Hz), 8.22 (d, 1 H, J=8.7 Hz); ms(fast atom bombardment): m/z 349 [M+H$^+$ ($^{37}$Cl)], 347 [M+H$^+$ ($^{35}$Cl)].

Anal. Calcd. for $C_{15}H_7ClN_2O_4S$: C, 51.96; H, 2.03; N, 8.08. Found: C, 51.38; H, 1.88; N, 8.27.

Example 2

Compound III, X=5-F, Y=6-Cl, R$^1$=2-Thienyl

A solution of 6-chloro-5-fluoro-3-(2-thenoyl)-2-oxindole (Preparation 1) (18.6 g, 0.063 mol) in anhydrous methylene chloride (1500 ml) was cooled in an ice bath. A solution of chlorocarbonyl isocyanate (5.0 ml, 0.062 mol) in anhydrous methylene chloride (20 ml) was then added dropwise with mechanical stirring. When addition of the chlorocarbonyl isocyanate solution was complete, stirring was continued at 0° C. for 1 hour and then at 20° C. for 18 hours. The mixture was filtered, washing well with methylene chloride, to collect the off-white, finely crystalline product III, X=5-fluoro, Y=6-chloro, R$^1$=2-thienyl, which was recrystallized from acetonitrile, 16.6 g (73%), mp>260° C.; ir (potassium bromide): v CO 1805, 1780 cm$^{-1}$; $^1$H nmr (perdeutedoacetone): δ7.28 (dd, 1 H, J=4.0, 5.0 Hz), 7.90 (d, 1 H, J=11.2 Hz), 8.00 (dd, 1 H, J=1.1, 5.0 Hz), 8.12 (dd, 1 H, J=1.1, 4.0 Hz), 8.31 (d, 1 H, J=7.3 Hz); ms (fast atom bombardment): m/z 367 [M+H$^+$ ($^{37}$Cl)], 365 [M+H$^+$ ($^{35}$Cl)].

Anal. Calcd. for $C_{15}H_6ClFN_2O_4S$: C, 49.40; H, 1.66; N, 7.68. Found: C, 49.21; H, 1.64; N, 7.84.

Example 3

General reaction of compounds of Examples 1 and 2 with alcohols to yield Compound I,Q=OR$^2$ A slurry of the compound of Example 2 (1.0 mg, 2.74 mmol) and triethylamine (0.42 ml, 3.03 mmol) in benzyl alcohol (16 ml) was warmed at 50° C. for 18 hours to give a homogeneous yellow solution. After pouring into 1N HCl, the mixture was extracted with methylene chloride. The methylene chloride extract was washed with water, dried over MgSO$_4$ and concentrated to leave an oil. Addition of ether resulted in crystallization of Compound 1, X=5-fluoro, Y=6-chloro, Q=benzyloxy, R$^1$=2-thienyl, as a yellow, finely crystalline solid, 745 mg (57%). Compound I, X=5-Cl, Y=H, R¹=2-thienyl, Q=ethoxy and octyloxy were similarly obtained by the reaction of the compound of Example 1 with ethanol and n-octanol respectively. Both compounds were recrystallized from acetonitrile.

Example 4

Compound I, X=5-F, Y=6-Cl, R¹=2-Thienyl, Q=(S)—OCH₂CH(CO₂H)NHBOC

A solution of the compound of Example 2 (570 mg, 1.56 mmol), diisopropylethylamine (0.78 ml, 4.5 mmol), and N-BOC-L-serine (923 mg, 4.50 mmol) in anhydrous 1,4-dioxane (3 ml) was heated at 50° C. for 18 hours. After pouring into 1N HCl, the mixture was extracted with methylene chloride. The methylene chloride extract was washed with water, dried over MgSO₄ and concentrated to leave a yellow foam. This was taken up in hot acetonitrile. On cooling, the title product precipitated as a yellow crystalline solid, 500 mg (56%).

Example 5

Compound I, X=5-F, Y=6-Cl, R¹=2-Thienyl, Q=OC₆H₅

Phenol (141 mg, 1.49 mmol) was added to a slurry of NaH (36 mg, 1.5 mmol) in anhydrous 1,2-dimethoxyethane (15 ml). After stirring for 15 minutes, the compound of Example 2 (570 mg, 1.56 mmol) was added and the mixture was warmed at 40° C. for 6 hours. After pouring into 1N HCl, the mixture was extracted with methylene chloride. The methylene chloride extract was washed with water, dried over MgSO₄ and concentrated to leave a yellow solid. This was recrystallized from acetonitrile to provide the title product as a yellow crystalline solid, 450 mg (63%).

Example 6

General reaction of the compounds of Examples 1 and 2 with amines to yield Compound I, Q=NR²R³ n-Butylamine (0.16 ml, 1.62 mmol) was added to a slurry of the compound of Example 1 (520 mg, 1.50 mmol) in methylene chloride (25 ml). The mixture was stirred at 20° C. for 18 hours. After pouring into 1N HCl, the mixture was extracted with methylene chloride. The methylene chloride extract was washed with water, dried over MgSO₄ and concentrated to leave a yellow solid. This was recrystallized from acetonitrile to give Compound I, R¹=2-thienyl, X=Cl, Y=H, Q=NH(CH₂)₃CH₃ as a yellow crystalline solid, 270 mg (43%). Compounds I, Q=NHCH₂Ph and N(ET)₂ were similarly obtained by the reactions of the compound of Example 1 with benzylamine and the compound of Example 2 with diethylamine to yield respectively Compound I, X=5-Cl, Y=H, R¹=2-thienyl, Q=NHCH₂Ph; and Compound I, X=5-F, Y=6-Cl, R¹=2-thi Q=N(ET)₂. Both compounds were recrystallized from acetonitrile.

Example 7

General reaction of the compound of Example 1 with amino acids

To a solution of the compound of Example 1 (520 mg, 1.50 mmol) and triethylamine (0.22 ml, 1.58 mmol) in N,N-dimethylformamide (20 ml) was added L-phenylalanine (264 mg, 1.60 mmol). The mixture was stirred at 20° C. for 18 hours. After pouring into 1N HCl, the mixture was extracted with methylene chloride. The methylene chloride extract was washed with water, dried over MgSO₄ and concentrated to leave an oil containing residual N,N-dimethylformamide. Most of this was removed by evaporation under high vacuum to Compound I, X=5-Cl, Y=H, R¹=2-thienyl, Q=NHCH(CO₂H)CH₂Ph, yield as a fine yellow powder, 450 mg (58%). The reaction of the compound of Example 1 was carried out with L-serine using the same procedure except that the crude product was triturated with methylene chloride to yield Compound I, X=5-Cl, Y=H, R¹=2-thienyl, Q=NHCH(CO₂H)CH₂OH.

TABLE I

Structures, Melting Points, Yields and Analytical Data for Compounds of Examples 3–7
R¹ = 2-Thienyl, Q = OR²

| Example | R² X,Y | Mp °C. | Yield (%) [a] | Formula | Analysis (Calcd./Found) C | H | N |
|---|---|---|---|---|---|---|---|
| 3a | Et<br>5-Cl, H | 203–205 | 73 | C₁₇H₁₃ClN₂O₅S | 51.98<br>52.13 | 3.34<br>3.25 | 7.13<br>7.29 |
| 3b | CH₂Ph<br>5-F, 6-Cl | 195–197 | 57[b] | C₂₂H₁₄ClFN₂O₅S | 55.88<br>55.90 | 2.98<br>2.76 | 5.92<br>5.84 |
| 3c | (CH₂)₇CH₃<br>5-Cl, H | 129–131 | 52 | C₂₃H₂₅ClN₂O₅S | 57.92<br>57.84 | 5.28<br>5.04 | 5.87<br>5.89 |
| 4 | (S)—CH₂CH—(CO₂H)—NHBOC<br>5-F, 6-Cl | 147–150 | 56 | C₂₃H₂₁ClFN₃O₉S | 48.47<br>48.00 | 3.71<br>3.41 | 7.37<br>7.32 |
| 5 | Ph<br>5-F, 6-Cl | 205–210 | 63 | C₂₁H₁₂ClFN₂O₅S | 54.97<br>54.61 | 2.64<br>2.40 | 6.10<br>6.21 |

[a]Except where indicated yields are of material recrystallized from acetonitrile.
[b]Crystallized from diethyl ether.

TABLE I-continued

Structures, Melting Points, Yields and Analytical Data for
Compounds of Examples 3–7
$R^1$ = 2-Thienyl, Q = $NR^2R^3$

| Example | $R^2 R^3$<br>X,Y | Mp °C. | Yield (%) | Formula | Analysis (Calcd./Found) C | H | N |
|---|---|---|---|---|---|---|---|
| 6a | $(CH_2)_3CH_3$, H<br>5-Cl, H | 162–164 | 43[a] | $C_{19}H_{18}ClN_3O_4S$ | 54.34<br>54.27 | 4.32<br>4.04 | 10.00<br>9.95 |
| 6b | $CH_2Ph$, H<br>5-Cl, H | 171–175 | 63[a] | $C_{22}H_{16}ClN_3O_4S$ | 58.22<br>58.14 | 3.55<br>3.38 | 9.26<br>9.29 |
| 6c | Et, Et<br>5-F, 6-Cl | 192–194 | 64[b] | $C_{19}H_{17}ClFN_3O_4S$ | 52.10<br>51.64 | 3.91<br>3.72 | 9.60<br>9.41 |
| 7a | (S)—$CH(CO_2H)$—$CH_2Ph$, H<br>5-Cl, H | 228–231 | 58[c] | $C_{24}H_{18}ClN_3O_6S$ | 56.31<br>56.01 | 3.54<br>3.34 | 8.21<br>8.26 |
| 7b | (S)—$CH(CO_2H)$—$CH_2OH$, H<br>5-Cl, H | 204–206 | 48[d] | $C_{18}H_{14}ClN_3O_7S$ | 47.85<br>47.63 | 3.12<br>2.84 | 9.30<br>9.18 |

[a]Recrystallized from acetonitrile.
[b]Purified by trituration with acetone.
[c]Purified by trituration with hot acetonitrile.
[d]Purified by trituration with $CH_2Cl_2$.

TABLE II $^1$H NMR, Mass and IR Spectroscopiic Data for Examples 3–5

| Example | $^1$H NMR (δ, ppm) | FAB MS m/z (MH$^+$) | IR (cm$^{-1}$) C=O (KBr) |
|---|---|---|---|
| 3a | (deuteriochloroform)1.37(t, 3H, J=7.2Hz), 4.34(q, 2H, J=7.2Hz), 7.25(dd, 1H, J=2.1, 8.8Hz), 7.31(dd, 1H, J=3.9, 5.0Hz), 7.65(d, 1H, J=2.1Hz), 7.81(dd, 1H, J=1.1, 5.0Hz), 7.95(dd, 1H, J=1.1, 3.9Hz), 8.34(d, 1H, J=8.8Hz), 11.0(brs, 1H). | 393 | 1800, 1725, 1656 |
| 3b | (deuteriochloroform)5.30(s, 2H), 7.30(dd, 1H, J=3.8, 5.0Hz), 7.36–7.47(m, 6H), 7.82(dd, 1H, J=1.1, 6.0Hz), 7.90(dd, 1H, J=1.1, 3.8Hz), 8.51(d, 1H, J=6.9Hz), 11.00(brs, 1H). | 473 | 1802, 1728, 1645 |
| 3c | (deuteriochloroform)0.89(t, 3H, J=6.9Hz), 1.25–1.40(m, 10H), 1.68–1.78(m, 2H), 4.26(t, 2H, J=6.8Hz), 7.25(dd, 1H, J-2.1, 8.8Hz), 7.32 (dd, 1H, J=4.0, 5.0Hz), 7.65(d, 1H, J=2.1Hz), 7.80(dd, 1H, J=1.0, 5.0Hz), 7.94(dd, 1H, J=1.0, 4.0Hz), 8.34(d, 1H, J=8.8Hz), 11.00(brs, 1H). | 477 | 1795, 1722, 1648 |
| 4 | (DMSO-$d_6$)1.39(s, 9H), 4.22(dd, 1H, J=7.2, 10.3Hz)4.30–4.40(m, 1H), 4.45(dd, J=3.5, 10.3Hz), 7.13(dd, 1H, J=3.9, 4.9Hz), 7.37(brd, 1H, J=8.0Hz), 7.69(dd, 1H, J=0.9, 4.9Hz), 8.02(d, 1H, J=11.4Hz), 8.10(d, 1H, J=7.2Hz), 8.46(dd, 1H, J=0.9, 3.9Hz), 12.82(brs, 1H). | 570 | 1798, 1725, 1653 |
| 5 | (deuteriochloroform)7.23–7.34(m, 4H), 7.40–7.52(m, 3H), 7.83(dd, 1H, J=1.1, 5.0Hz), 7.97(dd, 1H, J=1.1, 3.8Hz), 8.57(d, 1H, J=6.9Hz), 11.30(brs, 1H). | 459 | 1810, 1730, 1753 |

TABLE III $^1$H NMR, Mass and IR Spectroscopiic Data for Examples 6a–7b

| Example | $^1$H NMR(δ, ppm) | FAB MS m/z (MH$^+$) | IR (Cm$^{-1}$) C=O(KBr) |
|---|---|---|---|
| 6a | (deuteriochloroform)0.97(t, 3H, J=7.0Hz), 1.36–1.48(m, 2H0, 1.56–1.65(m, 2H), 3.35–3.41(m, 2H), 7.24(dd, 1H, J=2.1, 8.8Hz), 7.30 (dd, 1H, J=3.8, 5.0Hz), 7.67(d, 1H, J=2.1Hz), 7.81(dd, 1H, J=1.1, 5.0Hz), 7.94(dd, 1H, J-1.1, 3.8Hz), 8.02(brt, 1H), 8.23(d, 1H, J=8.8Hz), 10.60(brs, 1H). | 420 | 1715, 1700, 1650 |
| 6b | (deuteriochloroform)4.59(d, 2H, J=5.8Hz), 7.22(dd, 1H, J=2.2, 8.8Hz), 7.30(dd, 1H, J=3.9, 5.0Hz), 7.34–7.38(m, 5H), 7.67(d, 1H, J=2.2Hz), 7.81(dd, 1H, J=1.1, 5.0Hz), 7.94(dd, 1H), J=1.1, 3.9Hz), 8.20(d, 1H, J=8.8Hz), 8.40(brt, 1H), 10.74(br s, 1H). | 454 | 1722, 1693, 1658, 1610 |
| 6c | (DMSO-$d_6$)1.13(t, 6H, J=7.0Hz), 3.32(q, 4H, J=7.0Hz), 7.11(dd, 1H, J=3.8, 5.0Hz), 7.68(dd, 1H, J=1.1, 5.0Hz), 8.00(d, 1H, J=11.2Hz), 8.12(d, 1H, J=7.3Hz), 8.49(dd, 1H, J=1.1, 3.7Hz), 12.60(brs, 1H). | 438 | 1769, 1693, 1638 |
| 7a | (DMSO-$d_6$)3.06(dd, 1H, J=6.9, 12.8Hz), 3.17(dd, 1H, J=5.1, 13.8Hz), 4.55–4.63(m, 1H), 6.94(dd, J=2.3, 8.6Hz), 7.12(dd, 1H, J=3.8, 4.8Hz), 7.19–7.32(m, 5H), 7.69(d, 1H, J=4.8Hz), 7.94(d, 1H, J=8.6 | 512 | 1741, 1727, 1695, 1647 |

TABLE III-continued $^1$H NMR, Mass and IR Spectroscopic Data for Examples 6a–7b

| Example | $^1$H NMR($\delta$, ppm) | FAB MS m/z (MH$^+$) | IR (Cm$^{-1}$) C=O(KBr) |
|---|---|---|---|
| | Hz), 8.12(d, 1H, J=2.3Hz), 8.38(d, 1H, J=3.8Hz), 8.47(d, 1H, J=7.6Hz), 12.28(brs, 1H). | | |
| 7b | (DMSO-d$_6$)3.71(dd, 1H, J=3.5, 10.9Hz), 3.83(dd, 1H, J=3.3, 10.9Hz), 4.30–4.34(m, 1H0, 5.80(brs, 1H), 6.95(dd, J=2.3, 8.6Hz), 7.12(dd, 1H, J=3.8, 5.0Hz), 7.69(dd, 1H, J=1.1, 5.0Hz), 8.00(d, 1H, J=8.6Hz), 8.12(d, 1H, J=2.3Hz), 8.39(dd, 1H, J=1.1, 3.8Hz), 8.68(d, 1H, J=7.7Hz), 12.27(brs, 1H). | 452 | 1733(br), 1658(br) |

EXAMPLE 8

Following the general procedure of Example 3 employing as starting materials the compound of Example 2 and the appropriate alcohol using protecting groups if required, the following compounds of formula I were obtained: $R^1$=2-thienyl, X=5-fluoro, Y=6-chloro and Q=OR$^2$.

TABLE IV

| R$^2$ | Mp °C. | C | H | N |
|---|---|---|---|---|
| Et | 198–199 | 49.70 | 2.94 | 6.82 |
| | | 49.64 | 2.93 | 6.88 |
| Me | 203–205 | 48.43 | 2.54 | 7.06 |
| | | 48.38 | 2.24 | 6.98 |
| (CH$_2$)$_2$t-Bu | 190–192 | 54.02 | 4.32 | 6.00 |
| | | 54.03 | 4.03 | 5.95 |
| CH$_2$CONEt$_2$ | 207–209 | 50.86 | 3.86 | 8.47 |
| | | | 50.51 | 3.59 | 8.40 |
| (CH$_2$)$_2$NEt | 188–191 | 48.66 | 4.28 | 8.11 |
| | | 48.71 | 4.24 | 8.08 |
| CH(Me)CO$_2$Et | 156–158 | 49.75 | 3.34 | 5.80 |
| | | 49.73 | 2.95 | 5.90 |
| CH$_2$CONMe$_2$ | 204–205 | 48.78 | 3.23 | 8.98 |
| | | 48.40 | 2.86 | 8.84 |
| iPr | 202–204 | 50.89 | 3.32 | 6.68 |
| | | 50.83 | 2.95 | 6.51 |
| CH$_2$CH=CH$_2$ | 192–195 | 51.13 | 2.86 | 6.62 |
| | | 51.12 | 2.70 | 6.65 |
| 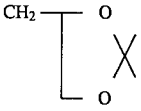 | 166–167 | 50.76 | 3.65 | 5.64 |
| | | 50.59 | 3.28 | 5.66 |
| CH$_2$CH(CO$_2$H)NH$_2$ | 170, 210 | 41.23 | 3.08 | 8.01 |
| | | 41.40 | 2.99 | 8.00 |
| (CH$_2$)$_2$Ph | 159–160 | 56.74 | 3.31 | 5.75 |
| | | 56.73 | 3.38 | 5.74 |
| CH$_2$(2-furyl) | 175 | 51.90 | 2.61 | 6.05 |
| | | 51.83 | 2.65 | 6.16 |
| farnesyl | 134–136 | 61.34 | 5.49 | 4.77 |
| | | 60.63 | 5.09 | 4.74 |
| CH$_2$CH$_2$CH$_2$CH=CH$_2$ | 169–170 | 53.28 | 3.58 | 6.21 |
| | | 53.18 | 3.42 | 6.14 |
| CH$_2$CH=C(CH$_3$)$_2$ | 178–180 | 53.28 | 3.58 | 6.21 |
| | | 52.90 | 3.44 | 6.29 |
| Cyclohexyl | 206–208 | 54.26 | 3.90 | 6.03 |
| | | 53.71 | 3.72 | 6.08 |
| n-propyl | 170–173 | 50.89 | 3.31 | 6.59 |
| | | 50.63 | 3.09 | 6.63 |
| 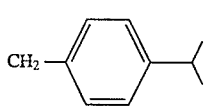 | 158–160 | 58.31 | 3.91 | 5.44 |
| | | 58.13 | 3.66 | 5.44 |
| 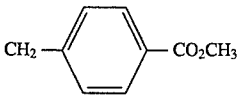 | 206–206 | 54.30 | 3.04 | 5.28 |
| | | 54.48 | 2.83 | 5.31 |
| 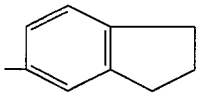 | 227–229 | 56.75 | 3.37 | 5.52 |
| | | 56.84 | 3.11 | 5.66 |

EXAMPLE 9

Following the general procedure of Example 6 or 7 employing as starting materials the compound of Example 2 and the appropriate amine, the following compounds of formula I were obtained: $R^1$=2-thineyl, X=5-fluoro, Y=6-chloro, Q=NR$^2$R$^3$=H.

TABLE V

| R$^2$ | Mp °C. | C | H | N |
|---|---|---|---|---|
| (CH$_2$)$_2$tBu | 170–172 | 54.14 | 4.54 | 9.02 |
| | | 53.94 | 4.30 | 8.96 |
| (CH$_2$)$_2$NMe$_2$ | 238–239 | 49.41 | 4.15 | 12.12 |
| | | 49.16 | 3.81 | 11.96 |
| n-Bu | 158–160 | 50.06 | 4.20 | 9.22 |
| | | 49.91 | 3.54 | 9.14 |
| CH$_2$CO$_2$H | 223–224 | 46.43 | 2.52 | 9.55 |
| | | 46.16 | 2.28 | 9.46 |
| CH$_2$Ph | 174–175 | 56.00 | 3.20 | 8.90 |
| | | 56.07 | 2.94 | 8.89 |
| n-Pr | 190–192 | 51.01 | 3.57 | 9.91 |
| | | 51.03 | 3.41 | 9.82 |
| CH(CO$_2$H)CH$_2$Ph | 225–227 | 53.95 | 3.30 | 7.86 |
| | | 53.73 | 3.05 | 7.75 |
| CH(CH$_2$OH)CO$_2$H | 210–211 | 46.02 | 2.79 | 8.94 |
| | | 45.89 | 2.62 | 8.78 |
| OH | 196–198 | 45.29 | 2.28 | 10.56 |
| | | 44.97 | 2.09 | 10.30 |

Example 10

Following the general procedure of Example 3 or 6 employing as starting materials the compound of Example 1 and the appropriate amine or alcohol, the following compounds of formula I were obtained $R^1$=2-thienyl, X=5-chloro, Y=H.

TABLE VI

| Q | Mp °C. | Analysis (Calcd./Found) | | |
|---|---|---|---|---|
| | | C | H | N |
| OMe | 192–194 | 50.73 | 2.93 | 7.39 |
| | | 50.69 | 2.66 | 7.41 |
| OBz | 161–164 | 58.09 | 3.32 | 6.16 |
| | | 58.09 | 3.06 | 6.16 |
| $NEt_2$ | 158–160 | 54.35 | 4.32 | 10.00 |
| | | 54.29 | 3.90 | 9.91 |
| OPh | 180–185 | 57.21 | 2.97 | 6.35 |
| | | 57.62 | 2.93 | 6.48 |

PREPARATION 1

3-(3-Furoyl)-2-oxindole

To a stirred solution of 2.8 g (0.12 mole) of sodium in 200 ml of ethanol was added 13.3 g (0.10 mole) of 2-oxindole, followed by 16.8 g of ethyl 3-furoate. The mixture was heated under reflux for 47 hours, cooled and then the solvent was removed by evaporation in vacuo. The residue was triturated under 200 ml of ether, and the solid was collected by filtration and discarded. The filtrate was evaporated in vacuo, and the residue triturated under diisopropyl ether and recovered by filtration. The solid was suspended in 250 ml of water, which was then acidified with concentrated hydrochloric acid. This mixture was stirred to give a solid, which was recovered by filtration. This latter solid was recrystallized from acetic acid followed by acetonitrile to give 705 mg of the title compound, mp 185°–186° C.

Analysis: Calcd. for $C_{13}H_9O_3N$: C, 68.72; H, 3.99; N, 6.17%. Found: C, 68.72; H, 4.14; N, 6.14%

Reaction of the appropriate 2-oxindole with the ethyl ester of the requisite carboxylic acid, substantially according to the above procedure, gave the following compounds:

5-chloro-3-(2-thenoyl)-2-oxindole, mp190.5°–192° C., 36% yield;

5-chloro-3-(2-furoyl)-2-oxindole, mp234°–235° C., 54% yield;

5-fluoro-3-(2-furoyl)-2-oxindole, mp222°–224° C., 51% yield;

5-fluoro-3-(2-thenoyl)-2-oxindole, mp200°–203° C., 26% yield;

6-fluoro-3-(2-furoyl)-2-oxindole, mp239°–242° C., 26% yield; and 6-chloro-5-fluoro-3(2-thenoyl)-2-oxindole, mp212°–215° C., 20% yield.

I claim:

1. A compound of the formula:

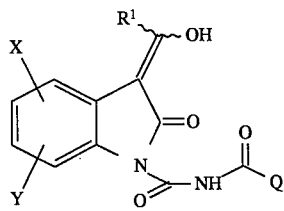

I wherein,

X is hydrogen, chlorine or fluorine;
Y is hydrogen, chlorine or fluorine;
$R^1$ is substituted or unsubstituted thienyl, furyl or phenyl;
Q is $OR^2$ or $NR^3R^4$; wherein
  $R^2$ is $C_1$–$C_{10}$ alkyl, $C_4$–$C_{10}$ cycloalkyl, phenyl, substituted phenyl, $C_5$–$C_{10}$ cycloalkenyl, $C_3$–$C_{10}$ alkenyl, $(CH_2)_mCH(R^5)CO_2R^6$, $(CH_2)_mCH(R^5)CONR^6R^7$, $(CH_2)_nCH(R^8)NR^5R^9$, farnesyl, geranyl, 6-indanyl, $CH_2$(2,2-dimethyl-1,3-dioxolan-4-yl), $(CH_2)_n$-2-thienyl, $(CH_2)_n$-3-thienyl, $(CH_2)_n$-3-furyl, $(CH_2)_n$-2-furyl, $(CH_2)_n$-2-pyridyl, $(CH_2)_n$-3-pyridyl, $(CH_2)_n$-4-pyridyl, $(CH_2)_n$-phenyl or $(CH_2)_n$-substituted phenyl;
  $R^3$ is hydrogen, $OR^5$, $C_1$–$C_{10}$ alkyl, $C_4$–$C_{10}$ cycloalkyl, phenyl, substituted phenyl, $C_3$–$C_{10}$ alkenyl, $C_5$–$C_{10}$ cycloalkenyl, $(CH_2)_mCH(R^{10})CO_2R^5$, $(CH_2)yNR^5R^9$, $(CH_2)_n$-phenyl, $(CH_2)_n$-substituted phenyl, $(CH_2)_n$-3-thienyl, $(CH_2)_n$-2-thienyl, $(CH_2)_n$-2-furyl, $(CH_2)_n$-3-furyl, $(CH_2)_n$-2-pyridyl, $(CH_2)_n$-3-pyridyl, or $(CH_2)_n$-4-pyridyl;
  $R^4$ is hydrogen, $C_1$–$C_{10}$ alkyl, $C_4$–$C_{10}$ cycloalkyl, phenyl, substituted phenyl, $C_3$–$C_{10}$ alkenyl, $C_5$–$C_{10}$ cycloalkenyl, $(CH_2)_yNR^5R^9$, $(CH_2)_n$-phenyl, $(CH_2)_n$-substituted phenyl, $(CH_2)_n$-2-thienyl, $(CH_2)_n$-3-thienyl, $(CH_2)_n$-2-furyl, $(CH_2)_n$-3-furyl, $(CH_2)_n$-2-pyridyl, $(CH_2)_n$-3-pyridyl, or $(CH_2)_n$-4-pyridyl;
  $R^5$, $R^6$ and $R^7$ are independently hydrogen, $C_1$–$C_6$ alkyl, benzyl, phenyl, allyl, $C_4C_8$ cycloalkyl;
  $R^8$ is hydrogen, $R^5$, $CO_2R^5$ or $CONR^5R^6$;
  $R^9$ is $R^5$, $C_1$–$C_6$ alkyl carbonyl, benzoyl, substituted benzoyl, benzyloxycarbonyl, or $C_1$–$C_6$ alkoxycarbonyl;
  $R^{10}$ is $C_1$–$C_6$ alkyl, $(CH_2)_nNR^5R^9$, $CH(CH_3)OR^5$, $CH_2OR^5$, $CH_2$-3-indolyl, $CH_2SR^5$, $CH_2$-p-$C_6H_4OR^5$, $(CH_2)_nSR^6$ or $(CH_2)_n$-3-imidazolyl;
  m is 0–6; n is 1–6; and y is 2–6; or a pharmaceutically acceptable salt thereof.

2. A compound of claim 1 wherein X is 5-chloro and Y is hydrogen.

3. A compound of claim 1 wherein X is 5-fluoro and Y is 6-chloro.

4. A compound of claim 3 wherein $R^1$ is 2-theinyl.

5. A compound of claim 2 wherein $R^1$ is 2-thienyl.

6. A compound of claim 4 wherein Q is $OR^2$ and $R^2$ is $C_1$–$C_6$ alkyl, benzyl or $(CH_2)_mCH(NHR^5)COOR^6$.

7. A compound of claim 6 wherein $R^2$ is $C_1$–$C_6$ alkyl.

8. The compound of claim 5 wherein $R^2$ is $(CH_2)_mCH(NHR^5)COOR^6$, m is 1, and $R^5$ and $R^6$ are hydrogen.

9. A compound of claim 4 wherein Q is $NR^3R^4$.

10. A compound of claim 9 wherein $R^2$ is $C_1$–$C_6$ alkyl or benzyl and $R^3$ is hydrogen or $C_1$–$C_6$ alkyl.

11. A compound of claim 9 wherein $R^3$ is $OR^5$.

12. The compound of claim 11 wherein $R^3$ and $R^5$ are hydrogen.

13. A method of treating inflammation in a mammal which comprises administering to said mammal an antiinflammatory effective amount of a compound of claim 1 or a pharmaceutically acceptable salt thereof.

14. A method of treating pain in a mammal which comprises administering to said mammal an analgesic effective amount of a compound of claim 1 or a pharmaceutically acceptable salt thereof.

15. A pharmaceutical composition comprising a pharmaceutically effective amount of a compound or a pharmaceutically acceptable salt thereof of claim 1 and a pharmaceutically acceptable inert carrier.

* * * * *